United States Patent [19]

Choe et al.

[11] Patent Number: 5,525,699

[45] Date of Patent: Jun. 11, 1996

[54] COPOLYMERS HAVING A CONTROLLED SEQUENCE STRUCTURE

[75] Inventors: Eui W. Choe, Randolph; Marie Borzo, Basking Ridge, both of N.J.

[73] Assignee: Hoechst Celanese Corp., Somerville, N.J.

[21] Appl. No.: 884,100

[22] Filed: May 15, 1992

[51] Int. Cl.$^6$ .................................................. C08G 73/00
[52] U.S. Cl. .................... 528/170; 528/125; 528/171; 528/183; 528/184; 528/190; 528/191; 528/193; 528/373
[58] Field of Search ..................... 528/125, 170, 528/171, 183, 184, 190, 191, 193, 373

[56] References Cited

U.S. PATENT DOCUMENTS 4,316,004   2/1982   Imai et al. ............................. 528/126

*Primary Examiner*—James J. Seidleck
*Assistant Examiner*—Terressa Mosley
*Attorney, Agent, or Firm*—P. S. Kalyanaraman

[57] ABSTRACT

A copolymer consisting essentially of a repeating sequence represented by the formula

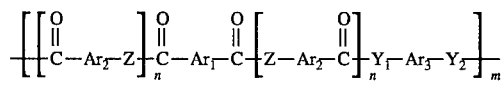

where $Ar_1$, $Ar_2$, and $Ar_3$, are each independently chosen from the group consisting of

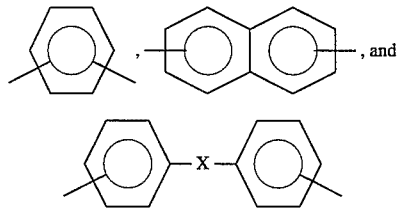 , and which are either unsubstituted or are substituted with one or more substituents chosen from the group consisting of alkyl groups having 1–6 carbon atoms, halogen (F, Cl or Br), and phenyl; Z, $Y_1$ and $Y_2$ are each independently O, NH, or S; n and m are positive integers; and X is a covalent bond, O, S, $SO_2$, CO, $C(C_6H_5)_2$, $C(C_6H_5)H$, $C(C_6H_5)(CH_3)$, $C(CH_3)_2$, $C(CH_3)H$, $CH_2$, $C(CF_3)_2$, or 3,3,5-trimethyl cyclohexyl. The polymers of this invention are derived from a minimum of three different monomers.

6 Claims, No Drawings

COPOLYMERS HAVING A CONTROLLED SEQUENCE STRUCTURE

BACKGROUND OF THE INVENTION

This invention relates to the field of copolymers, especially to copolymers having repeating units arranged in a regularly repeating sequence.

The subject matter of this invention is related to that of an application filed on the same date entitled "Condensation Copolymers With Sequenced Monomer Structure", and designated Docket Number 1464.

In common polymerization methods, monomers are combined in the reaction vessel and allowed to react at random. Unless there is only one way that the polymer can form, sequences of repeating monomeric units in the copolymer will be random.

Random sequences are expected whenever a polymer is formed from two different monomers that have the same functional groups. An example of such a random copolymer is a copolyester made from two monomers which each have a hydroxy and a carboxyl functionality, or a copolyamide in which each monomer has an amine and a carboxyl functionality. Another example is where more than two different monomers are combined, e.g. when two diols and one diacid form a polyester.

Ordered sequences are ordinarily expected only in polymers made from a single monomer, or from two monomers that have different functionalities, e.g., when a diol and a diacid form a polyester.

Controlled sequences are known to occur in biological processes where specific complex molecules act as templates or sequence controllers, e.g., DNA or RNA control in the growth of proteins. However, molecules are not available which similarly control the sequence of synthetic copolymers of the type described herein.

In block copolymers, different polymer sequences are formed as prepolymers and these prepolymers are then bonded together to form a polymer in which different regions in the polymeric chain exhibit different properties.

SUMMARY OF THE INVENTION

The present invention comprises a copolymer consisting essentially of a repeating sequence represented by the formula

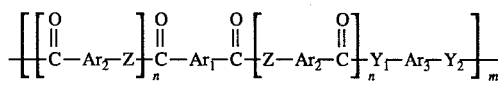

where $Ar_1$, $Ar_2$, and $Ar_3$, are each independently chosen from the group consisting of

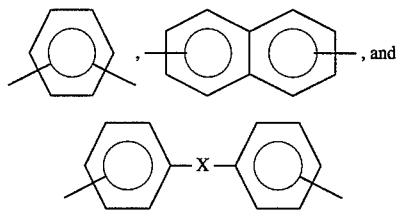

which are either unsubstituted or are substituted with one or more substituents chosen from the group consisting of alkyl groups having 1–6 carbon atoms, halogen (F, Cl or Br), and phenyl; Z, $Y_1$ and $Y_2$ are each independently O, NH, or S; n and m are positive integers; and X is a covalent bond, O, S, $SO_2$, CO, $C(C_6H_5)_2$, $C(C_6H_5)H$, $C(C_6H_5)(CH_3)$, $C(CH_3)_2$, $C(CH_3)H$, $CH_2$, $C(CF_3)_2$, or 3,3,5-trimethyl cyclohexyl. At least three different monomers are used to form the polymer.

It is an object of the present invention to provide a novel copolymer having a regularly repeating sequence.

It is another object of the present invention to provide a method for making a copolymer consisting essentially of repeating units arranged in a predetermined sequence.

Other objects and advantages of the present invention will be apparent to those skilled in the art from the following description and the appended claims.

DETAILED DESCRIPTION OF THE PREFERRED EMBODIMENTS

In one preferred embodiment of the present invention, an aromatic polyester having a controlled, regular, repeating sequence is formed from a diol (A), a dicarboxylic acid (B), and a hydroxycarboxylic acid (C). The diol is reacted with the hydroxycarboxylic acid in a mole ratio of one to two, respectively, to form a trimer (CAC) in which the hydroxyl groups of the two hydroxycarboxylic monomers are at the ends. This trimer is then reacted with the dicarboxylic acid to form a polymer having monomer units in the sequence $(—ACBC—)_x$.

Alternatively, two hydroxycarboxylic acid monomers could be reacted with one dicarboxylic acid monomer to achieve a trimer having acid end groups (CBC) which is then reacted with the diol to form the same sequenced polymer as in the first process.

Conventional polymerization methods are used to react the monomer, and the proper reaction conditions and catalyst (if any) are selected depending upon the monomers being polymerized. Sometimes it is preferable to convert a monomer to a derivative, e.g., an acid group may be converted to an acid chloride group, to facilitate the polymerization reaction. Those skilled in the art will be able to select an appropriate procedure without undue experimentation.

It is understood that in forming the trimers mentioned above, or any other prepolymer species according to this invention, some side products and unreacted monomers may be present; conventional separation methods are used to isolate the desired species. This is important since control of the final polymer product depends on using pure reactants. Those skilled in the art will know how to purify the desired species without undue experimentation.

The present invention also includes regularly sequenced polyamides that are formed from a diamine (A), a dicarboxylic acid (B), and an amino acid (C). This is accomplished by forming a trimer (CAC or CBC) which is then reacted with the third monomer (B or A) to form the polymer having monomer units in the sequence $(—ACBC—)_x$. Generally, CAC is more difficult to prepare then CBC due to unwanted side reactions.

In the same way, sulfur-containing polymers may be sequenced; e.g., where the amine groups in the monomers of the prior embodiment are replaced by sulfide groups. Mixed polymers can also be formed using monomers having a combination of amine, sulfide, and/or hydroxyl groups in reaction with dicarboxylic acid monomers.

For example, if a trimer formed from two hydroxycarboxylic acid monomers and one diol monomer is reacted with a trimer formed from two aminocarboxylic acid monomers and one dicarboxylic acid monomer, a polymer will be formed that has a regularly repeating sequence in which amide and ester linkages alternate in the pattern: 2 amide linkages, 4 ester linkages, 2 amide linkages, 4 ester linkages, etc. Replace the diacid with a diamine and replace the diol with a diacid in this example and a polymer will be obtained having a controlled sequence structure in which four amide linkages alternate with two ester linkages.

The prepolymer units that are ultimately combined to form the final polymer do not have to be trimers and monomers, but could be other species calculated to achieve a desired sequence. For example, in the case of a polyester such as that in the first embodiment described above, two additional moles of hydroxycarboxylic acid could have been reacted with either the trimer (CAC) to form a pentamer or with the acid monomer (B) to form a second trimer, to achieve a final polymer sequence of (—ACCBCC—)$_x$. If both the second trimer and the pentamer are formed and are reacted with each other, a polymer having this sequence is formed: (—ACCCBCCC—)$_x$.

Generically, the present invention comprises a copolymer consisting essentially of a repeating sequence represented by the formula

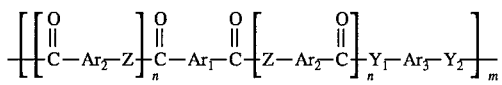

where $Ar_1$, $Ar_2$, and $Ar_3$, are each independently chosen from the group consisting of

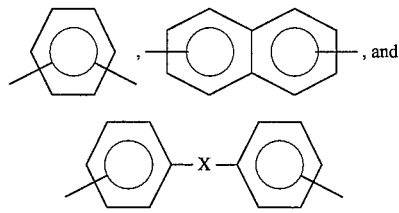

which are either unsubstituted or are substituted with one or more substituents chosen from the group consisting of alkyl groups having 1–6 carbon atoms, halogen (F, Cl or Br), and phenyl; Z, $Y_1$ and $Y_2$ are each independently O, NH, or S; n and m are positive integers; and X is a covalent bond, O, S, $SO_2$, CO, $C(C_6H_5)_2$, $C(C_6H_5)H$, $C(C_6H_5)(CH_3)$, $C(CH_3)_2$, $C(CH_3)H$, $CH_2$, $C(CF_3)_2$, or 3,3,5-trimethyl cyclohexyl. The polymers of this invention are derived from a minimum of three different monomers.

A key to controlling the sequence of the final polymer is to react two prepolymer species, whether monomers, trimers, or otherwise, which can only link in one way. In particular, if in each of the two reactant species the same functional group is at each end of the molecule, e.g., one species is a diol and the other a diacid, so that neither species can react with another molecule of the same species, then a polymer is created which necessarily has a regularly alternating pattern. The exact monomer sequence is controlled by the choice of the prepolymer species; one can build pepolymer reactants, e.g., trimers, to achieve a desired final polymer sequence.

Although randomly sequenced polymers are suitable for many purposes, in some cases it may be desirable to control the sequence structure of the polymer. The properties of the polymer may vary as the sequence changes. If the sequence of a polymer is controlled, a polymer having more reproducible properties may result. Furthermore, where a significant difference in properties accompanies sequence changes, a tailor-made polymer according to the present invention may be needed to achieve a desired result.

The copolymers of the present invention are useful for making high performance fibers, films and other articles having improved mechanical properties. These products may also exhibit significant permeability for gases and liquids, and therefore be useful in membrane or filtration applications.

The following non-limiting Examples illustrate several embodiments of the present invention. However, these Examples are only intended as illustrative, and the scope of the present invention is not limited to the embodiments illustrated herein; the scope of the present invention encompasses the entire subject matter covered by the appended claims.

EXAMPLE I

Preparation of di(p-carboxyphenyl)isophthalate

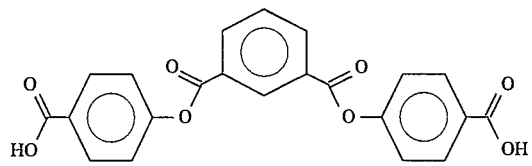

In a 10 liter three-necked Morton flask equipped with nitrogen inlet and outlet, thermometer, condenser and mechanical stirrer, were placed 179.6 grams (4.4 moles) of sodium hydroxide, 289.8 grams (2.1 m) of p-hydroxybenzoic acid, and 3 liters of distilled water. Isophthaloyl dichloride (203 grams, 1 m) was dissolved in 3 liters of methylene chloride. The acid chloride solution was added into the reaction flask with fast agitation. The resulting mixture was stirred at room temperature for one hour, and the solid disodium salt of the product was filtered, washed with water, and then acidified with a 10% solution of hydrochloric acid. The crude product was filtered, washed three times with distilled water, and twice with hot methanol, and then dried at 100° C. to obtain 300 grams of di(p-carboxyphenyl)isophthalate in 74% yield, with a melting point of 290°–300° C.

EXAMPLE II

Preparation of di(p-chlorocarbonylphenyl)isophthalate

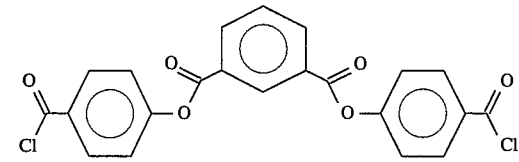

In a 2 liter three-necked flask equipped with nitrogen inlet and outlet, thermometer, condenser, safety trap, scrubber containing sodium hydroxide solution, and mechanical stirrer, were placed 100 grams (0.246 m) of di(p-carboxyphenyl)isophthalate, 1500 grams of thionyl chloride and 5 ml of N,N-dimethylformamide. The resulting mixture was reacted at about 80° C. for 24 hours, and cooled; a white solid was produced. The white solid was filtered, washed with hexanes, and dried. This white crude acid chloride was recrystallized from 5 liters of toluene, and dried at 100° C. under reduced pressure for 16 hours, to obtain 77 grams of di(p-chlorocarbonylphenyl)isophthalate in 71% yield: m.p. 204° C.; soluble in N-methyl-2-pyrrolidone, methylene chloride, dimethylsulfoxide, and hot toluene; insoluble in hexanes and cold toluene.

EXAMPLE III

Preparation of copolyester from di(p-chlorocarbonylphenyl)isophthalate and hydroquinone

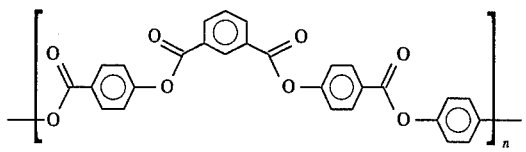

In a 12 liter three-necked Morton flask equipped with nitrogen inlet and outlet, thermometer, condenser and mechanical stirrer, were placed 22.15 grams (0.05 m) of di(p-chlorocarbonylphenyl)isophthalate, and 4.55 liters of methylene chloride. Hydroquinone (5.5 grams, 0.05 m) and 4.33 grams (0.105 m) of sodium hydroxide were dissolved in 300 ml of distilled water. This solution was added into the flask, along with an aqueous solution (50 ml) containing 0.7 grams of a 40% by weight benzyltrimethylammonium hydroxide solution in water. The resulting reaction mixture was stirred at 500 rpm at ambient temperature for 16 hours. Methylene chloride was then decanted. The solid polymer was filtered, washed twice with water, and air dried, washed twice with 400 ml of acetone, and then once more with water, and dried at 100° C. to obtain 17.13 grams of polymer with an inherent viscosity of 0.91 dl/g as determined at 0.1% concentration in HFIP/PFP 50/50 by volume at 25° C. The polymer exhibited a crystal to nematic transition at about 380° C., and a nematic to isotropic transition at about 480° C. Spectral analysis by NMR confirmed the structure of the polymer.

EXAMPLE IV

Preparation of copolyesteramide from di(p-chlorocarbonylphenyl)isophthalate and m-phenylenediamine

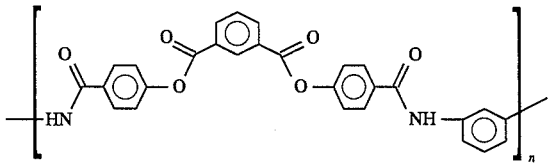

In a 2 liter three-necked resin flask equipped with nitrogen inlet and outlet, thermometer, condenser and mechanical stirrer, were placed 5.4 grams (0.05 m) of m-phenylenediamine, 4.3 grams of anhydrous lithium chloride, and 216 grams of N-methyl-2-pyrrolidone. The resulting mixture was cooled to −15° C. Di(p-chlorocarbonylphenyl)isophthalate (22.15 grams, 0.05 m) was added into the flask with fast agitation. The reaction temperature was allowed to rise to ambient temperature after the addition of the acid chloride. The resulting mixture was stirred for 5 hours at ambient temperature. The polymer was precipitated by adding the mixture to distilled water in a blender. The precipitated polyesteramide was filtered, washed with water, and dried at 100° C. and 0.1 Torr to obtain polyesteramide with a melting point of 405° C. and an inherent viscosity of 0.68 dl/g as determined at 0.1% concentration in HFIP/PFP 50/50 by volume at 25° C. The expected structure was confirmed by NMR spectral analysis.

EXAMPLE V

Preparation of copolyesteramide from di(p-chlorocarbonylphenyl)isophthalate and p-phenylenediamine

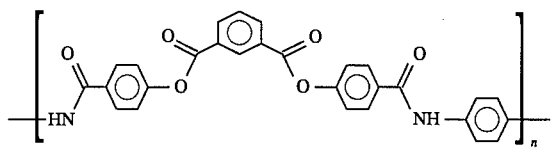

This copolyesteramide containing a p-phenyleneamide moiety was prepared in accordance with the procedure of Example IV, except that p-phenylenediamine was used instead of m-phenylenediamine, to obtain the copolyesteramide in 96.5% yield, with a melting point of 433° C. and the heat of fusion of 149 j/g as determined by DSC at a heating rate of 10° C. per minute under nitrogen.

EXAMPLE VI

Preparation of copolyesteramide from di(p-chlorocarbonylphenyl)isophthalate and aminophenol

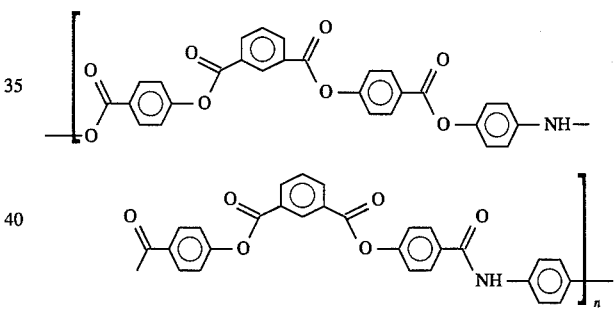

In a 2 liter three-necked resin flask equipped with nitrogen inlet and outlet, thermometer, condenser and mechanical stirrer, are placed 10.90 grams (0.1 m) of p-aminophenol, 4.3 grams of anhydrous lithium chloride, and 216 grams of N-methyl-2-pyrrolidone. The resulting mixture is cooled to −15° C. Di(p-chlorocarbonylphenyl)isophthalate (22.15 grams, 0.05 m) is added into the flask with fast agitation. The reaction temperature is allowed to rise to ambient temperature after the addition of the acid chloride. The resulting mixture is stirred for 5 hours at ambient temperature. The product aromatic esteramidediphenol is precipitated by adding the mixture to distilled water. The precipitated esteramidediphenol is filtered, washed with water, and dried at 100° C. and 0.1 Torr to obtain esteramidediphenol of formula

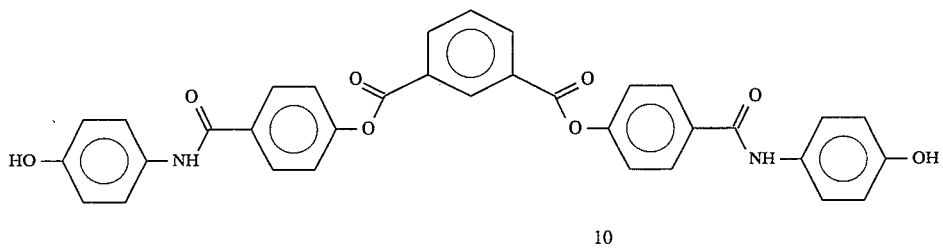

The copolyesteramide containing a p-phenyleneamideester moiety is prepared in accordance with the procedure of Example III, except that the esteramidediphenol is used instead of hydroquinone, to obtain the copolyesteramide.

EXAMPLE VII

Preparation of di (6-carboxy-2-naphthyl)isophthalate

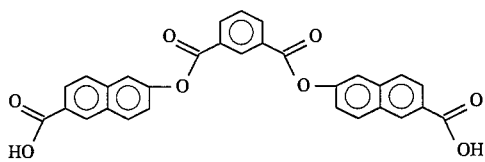

Di(6-carboxy-2-naphthyl)isophthalate was prepared in 78% yield in accordance with the procedure of Example I, except that 6-hydroxy-2-naphthoic acid was used instead of p-hydroxybenzoic acid. The compound melted at 340°–350° C.

EXAMPLE VIII

Preparation of di(6-chlorocarbonyl-2-naphthyl)isophthalate

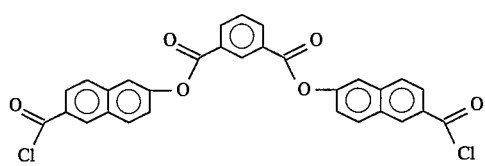

The acid chloride is prepared in accordance with the procedure of Example II, except that di(6-carboxy-2-naphthyl)-isophthalate is used instead of di(p-carboxyphenyl)isophthalate. This compound can be used for the preparation of controlled sequenced polymers in accordance with Examples III to VI.

Many variations and equivalents of the present invention will occur to those skilled in the art. The present invention is not limited to the embodiments illustrated or described, but includes all the subject matter within the spirit and scope of the appended claims and of the foregoing disclosure.

We claim:

1. A polyamide copolymer consisting essentially of a repeating sequence represented by the formula

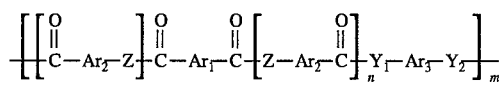

where $Ar_1$, $Ar_2$, and $Ar_3$ are each independently a member selected from the group consisting of

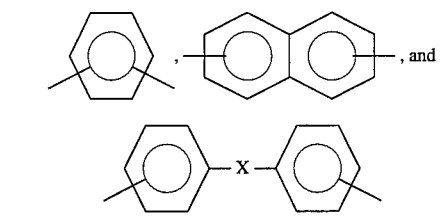

which are either unsubstituted or are substituted with one or more substitutents which substituent is a member selected from the group consisting of alkyl groups having 1–6 carbon atoms, halogen (F, Cl or Br), phenyl; Z is O, NH, or S; $Y_1$ and $Y_2$ are independently O or NH wherein both $Y_1$ and $Y_2$ are not O simultaneously; n and m are positive integers; and X is a covalent bond, O, S, $SO_2$, CO, $C(C_6H_5)(CH_3)$, $C(CH_3)_2$, $C(CH_3)H$, $CH_2$, $C(CF_3)_2$, or 3,3,5-trimethylcyclohexyl.

2. A copolymer according to claim 1 containing a repeating unit derived from aminophenol.

3. A copolymer according to claim 1 containing a repeating unit derived from phenyl diamine.

4. A process for preparing a copolyester consisting essentially of a repeating sequence represented by the formula

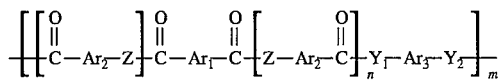

where $Ar_1$, $Ar_2$, and $Ar_3$ are each independently a member selected from the group consisting of

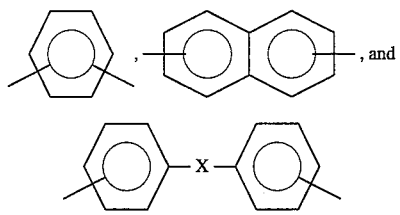

which are either unsubstituted or are substituted with one or more substitutents which substituent is a member selected from the group consisting of alkyl groups having 1–6 carbon atoms, halogen (F, Cl or Br), phenyl; Z is O, NH, or S; Z, $Y_1$ and $Y_2$ are each independently O, NH or S; n and m are positive integers; and X is a covalent bond, O, S, $SO_2$, CO, $C(C_6H_5)(CH_3)$, $C(CH_3)_2$, $C(CH_3)H$, $CH_2$, $C(CF_3)_2$, or 3,3,5-trimethylcyclohexyl, said process comprising:

reacting two parts of a hydroxycarboxylic acid with one part of a diol to form a trimeric species having two pendant hydroxyl groups; and, reacting said trimeric species with a dicarboxylic acid to form said copolyester.

5. A process for preparing a copolyamide according to claim 1 comprising:

reacting two parts of an aminocarboxylic acid with one part of a diamine to form a trimeric species having two pendant amine groups; and, reacting said trimeric species with a dicarboxylic acid to form said copolyamide.

6. A process for preparing a copolyamide according to claim 1 comprising:

reacting two parts of an aminocarboxylic acid with one part of a dicarboxylic acid to form a trimeric species having two pendant carboxyl groups; and, reacting said trimeric species with a diamine to form said copolyamide.

* * * * *